(12) United States Patent
Chu (10) Patent No.: US 9,962,176 B2
(45) Date of Patent: May 8, 2018

(54) RETRIEVAL DEVICES AND RELATED METHODS OF USE

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 439 days.

(21) Appl. No.: 14/593,594

(22) Filed: Jan. 9, 2015

(65) Prior Publication Data

US 2015/0196311 A1 Jul. 16, 2015

Related U.S. Application Data

(60) Provisional application No. 61/938,311, filed on Feb. 11, 2014, provisional application No. 61/925,952, filed on Jan. 10, 2014.

(51) Int. Cl.
*A61B 17/22* (2006.01)
*A61B 17/221* (2006.01)
*B25J 1/02* (2006.01)

(52) U.S. Cl.
CPC .......... *A61B 17/221* (2013.01); *B25J 1/02* (2013.01); *A61B 2017/2212* (2013.01); *A61B 2017/2215* (2013.01)

(58) Field of Classification Search
CPC .......... A61B 17/221; A61B 2017/2212; A61B 2017/2215; A61B 17/22031; A61B 2017/00358; A61B 2017/22035; A61B 2017/301; B25J 1/02

USPC .......................................................... 606/127
See application file for complete search history.

(56) References Cited

U.S. PATENT DOCUMENTS

| | | | |
|---|---|---|---|
| 5,201,741 A * | 4/1993 | Dulebohn | A61B 17/32056 606/110 |
| 5,906,622 A | 5/1999 | Lippitt et al. | |
| 5,924,175 A * | 7/1999 | Lippitt | A61B 17/221 24/537 |
| 6,458,145 B1 | 10/2002 | Ravenscroft et al. | |
| 6,626,915 B2 | 9/2003 | Leveillee | |
| 7,041,108 B2 | 5/2006 | Lippitt et al. | |

(Continued)

FOREIGN PATENT DOCUMENTS

| | | |
|---|---|---|
| WO | WO 98/48710 A1 | 11/1998 |
| WO | WO 99/16363 A1 | 4/1999 |

*Primary Examiner* — Diane Yabut
*Assistant Examiner* — Martin T Ton
(74) *Attorney, Agent, or Firm* — Bookoff McAndrews, PLLC (57) ABSTRACT

According to an example of the present disclosure, a retrieval device having a contracted state and an expanded state may include at least three support members each having a lumen, a fixed proximal end, and a movable distal end, and at least two members movable relative to the support members. Each movable member may include a first end and a second end and extending distally through a lumen of a support member and proximally through a lumen of a different support member. The device may include a stop located at the second end of at least one movable member to restrict movement of the second end after moving a distance distally during movement of the retrieval device toward the expanded state.

20 Claims, 7 Drawing Sheets

(56) References Cited

U.S. PATENT DOCUMENTS

| | | |
|---|---|---|
| 7,210,210 B2 | 5/2007 | Lippitt et al. |
| 2001/0047169 A1 | 11/2001 | McGuckin, Jr. et al. |
| 2004/0215212 A1* | 10/2004 | Teague ................. A61B 17/221 |
| | | 606/127 |

* cited by examiner

RETRIEVAL DEVICES AND RELATED METHODS OF USE

CROSS-REFERENCE TO RELATED APPLICATIONS

This patent application claims benefit of priority under 35 U.S.C. § 119 to U.S. Provisional Patent Application No. 61/938,311, filed Feb. 11, 2014, and to U.S. Provisional Patent Application No. 61/925,952, filed Jan. 10, 2014, the entireties of each of which is incorporated herein by reference.

TECHNICAL FIELD

Various examples of the present disclosure relate generally to retrieval devices and related systems and methods. More specifically, the present disclosure relates to devices, systems, and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Further, lithotripsy and ureteroscopy, for example, are used to treat urinary calculi (e.g., kidney stones) in the ureter of a patient.

Retrieval devices may include end effectors for manipulating objects. An exemplary end effector may have a plurality of arms that support a front loop that forms when the end effector is opened. The size of the front loop may limit the size of an object that can be captured, repositioned, and/or released from the end effector. For some procedures, there may be a need to increase the size of a front loop of an end effector to facilitate the capturing, repositioning, and/or releasing of larger objects. It may also be desirable to have an end effector close back down to a low-profile state to facilitate insertion and withdrawal of the end effector into and from a target area, and/or to capture, reposition, and/or release smaller objects. Thus, there remains a need for retrieval devices with improved capabilities.

Further, known medical retrieval devices are complex, requiring many components and labor-intensive manufacturing processes. The assembly of small parts often requires visual magnification and specialized training. The available joining mechanisms often increase the profile of the medical retrieval devices beyond optimal design parameters, and are often the weakest structural points. These drawbacks result in medical retrieval devices that are bulky, expensive, and prone to failure.

Thus, there remains a need for improved medical retrieval devices having reduced profiles and fewer components.

SUMMARY

Examples of the present disclosure relate to, among other things, retrieval devices and related systems and methods. Each of the examples disclosed herein may include one or more of the features described in connection with any of the other disclosed examples.

According to an example of the present disclosure, a retrieval device having a contracted state and an expanded state may include at least three support members each having a lumen, a fixed proximal end, and a movable distal end, and at least two members movable relative to the support members. Each movable member may include a first end and a second end and extending distally through a lumen of a support member and proximally through a lumen of a different support member. The device may further include a stop located at the second end of at least one movable member to restrict movement of the second end after moving a distance distally during movement of the retrieval device toward the expanded state.

The at least two movable members may include three movable members. The stop may include a coupling securing the second ends of the at least two movable members together. The coupling may include a tube surrounding the second ends. Each of the movable members may include a preformed U-shaped bend located distally of the movable distal ends of the support members. The U-shaped bend may urge the support members toward the contracted state. The U-shaped bend may be located said distance from the movable distal end when the movable stop is abutting the fixed proximal end of the at least one support member. The movable members may form a first stage grasper when the U-shaped bend is located said distance from the movable distal end. The support members may extend generally parallel to one another during movement of the stop distally toward the expanded state. The device may include a sheath fixedly coupled to the proximal end of each of the support members, the sheath extending proximally to encompass at least a portion of the movable members.

According to another example, a retrieval device having a contracted state and an expanded state may include at least three support members each having a lumen, a fixed proximal end, and a movable distal end, and at least three members movable relative to the support members. Each movable member may include a first end and a second end and extending distally through a lumen of a support member and proximally through a lumen of a different support member. The device may further include a stop for the movable members, the stop including a coupling of the second ends of each of the movable members together at a spaced distance from the fixed proximal ends of the support members.

The coupling of the second ends may include securing the second ends in a tube. The stop may be located the spaced distance from the fixed proximal ends of the support members when the device is in a fully contracted state, and the spaced distance may be reduced during movement of the device toward the expanded state. The first end may be located distally of the second end. Each of the movable members may include a preformed U-shaped bend located distally of the movable distal ends of the support members. The U-shaped bend may urge the support members toward the contracted state. The U-shaped bend may be located a fixed distance from the stop and may move with the stop. The movable members may form a first stage grasper during initial movement toward the expanded state. The support members may extend generally parallel to one another during movement of the movable stop toward the expanded state.

According to yet another example, a method for retrieving an object using a retrieval device is disclosed. The retrieval device may include at least three tubular support members each having a fixed proximal end and a movable distal end. At least two members may be movable relative to the support members. Each movable member may include a first end and a second end and extending distally through a support member and proximally through a different support member. A stop may be located at the second end of at least one movable member. The method may include moving the first and second ends of the movable members distally until the stop restricts further movement of the second ends. The method also may include further moving the first ends of the movable members distally to expand the movable distal ends of the support members radially.

In one aspect, the present disclosure may be directed to a medical device. The medical device may include a plurality of branch members having a proximal end and a distal end. The medical device may also include a first movable member, and a second movable member. The plurality of branch members and the first and second movable members may form a basket movable between a collapsed configuration and an expanded configuration, and the entireties of the first and second movable members may be configured to move distally with respect to the plurality of branch members.

The first movable member may include a first bend disposed proximal to the proximal ends of the plurality of branch members, and the second movable member may include a second bend disposed proximal to the proximal ends of the plurality of branch members. The first bend may include a bend disposed at a middle portion of the first movable member; and the second bend may include a bend disposed at a middle portion of the second movable member. The first bend may encompass a midpoint of the first movable member, and the second bend may encompass a midpoint of the second movable member. In the collapsed configuration, the first and second bends may be separated from the proximal ends of the plurality of branch members by a first distance. The device may further include a drive member disposed proximally of the first and second movable members, wherein the first movable member has a first leg and a fourth leg, the second movable member has a first leg and a fourth leg, and a distal end of the drive member is coupled to the first and fourth legs of the first and second movable members. The first and fourth legs of the first and second movable members may each be disposed in a different branch member of the plurality of branch members. The drive member may be advanced distally by the first distance to move the medical device to an intermediate configuration between the collapsed configuration and the expanded configuration. In the intermediate configuration, the first and second bends may be engaged with the proximal ends of the plurality of branch members; After the first and second bends are engaged with the proximal ends of the plurality of branch members, further distal movement of the drive member may cause each of the first and fourth legs of the first and second movable members to extend distally through a respective branch member of the plurality of branch members. The first and fourth legs of the first and second movable members may each extend from a distal end of a respective branch member of the plurality of branch members to form a branch that extends into an adjacent branch member. A proximal retraction of the drive member while the medical device is in the expanded configuration may cause the first and fourth legs of the first and second movable members to retract proximally. The first and second bends may disengage from the proximal ends of the plurality of branch members during movement of the medical device from the expanded configuration to the collapsed configuration. The first and second bends may be engaged with the proximal ends of the plurality of branch members when the medical device is in the expanded configuration. The first movable member may include a second leg and a third leg, the second movable member may include a second leg and a third leg, and each of the second and third legs of the first and second movable members may be disposed in a different branch member of the plurality of branch members. The first and fourth legs of the first movable member and the second and third legs of the first movable member may each be disposed in a different branch member of the plurality of branch members, and the first and fourth legs of the second movable member and the second and third legs of the second movable member may each be disposed in a different branch member of the plurality of branch members. The proximal ends of the plurality of branch members may be coupled to one another. The device may include a sheath coupled to the proximal end of each of the plurality of branch members, the sheath extending proximally to encompass at least a portion of the first and second movable members.

In another aspect, the present disclosure is directed to a medical device. The medical device may include a plurality of branch members having a proximal end and a distal end, and a first movable member having a first bend disposed proximal to the proximal ends of each of the plurality of branch members. The medical device may include a second movable member having a second bend having a second bend disposed proximal to the proximal ends of each of the plurality of branch members. The plurality of branch members and the first and second movable members may form a basket movable between a collapsed configuration and an expanded configuration, and the first bend may be configured to engage with the proximal ends of a first pair of the plurality of branch members. The second bend may be configured to engage with the proximal ends of a second pair of the plurality of branch members, and branch members of the first pair and second pairs of the plurality of branch members may alternate with one another.

In yet another aspect, the present disclosure is directed to a medical device. The medical device may include a plurality of branch members having a proximal end and a distal end, and a first movable member having a first bend disposed proximal to the proximal ends of each of the plurality of branch members, The medical device may also include a second movable member having a second bend having a second bend disposed proximal to the proximal ends of each of the plurality of branch members. The plurality of branch members and the first and second movable members may form a basket movable between a collapsed configuration and an expanded configuration, and the first bend may be configured to engage with the proximal ends of a first pair of the plurality of branch members. The second bend may be configured to engage with the proximal ends of a second pair of the plurality of branch members.

It is understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Overview

The present disclosure is drawn to retrieval devices and related systems and methods. Reference will now be made in detail to examples of the present disclosure, examples of which are illustrated in the accompanying drawings. Wherever possible, the same reference numbers will be used throughout the drawings to refer to the same or like parts. The term "distal" refers to a portion farthest away from a user when introducing a device into a patient. By contrast, the term "proximal" refers to a portion closest to the user when placing the device into the patient.

EXAMPLES

Figures 1, 2, 3:
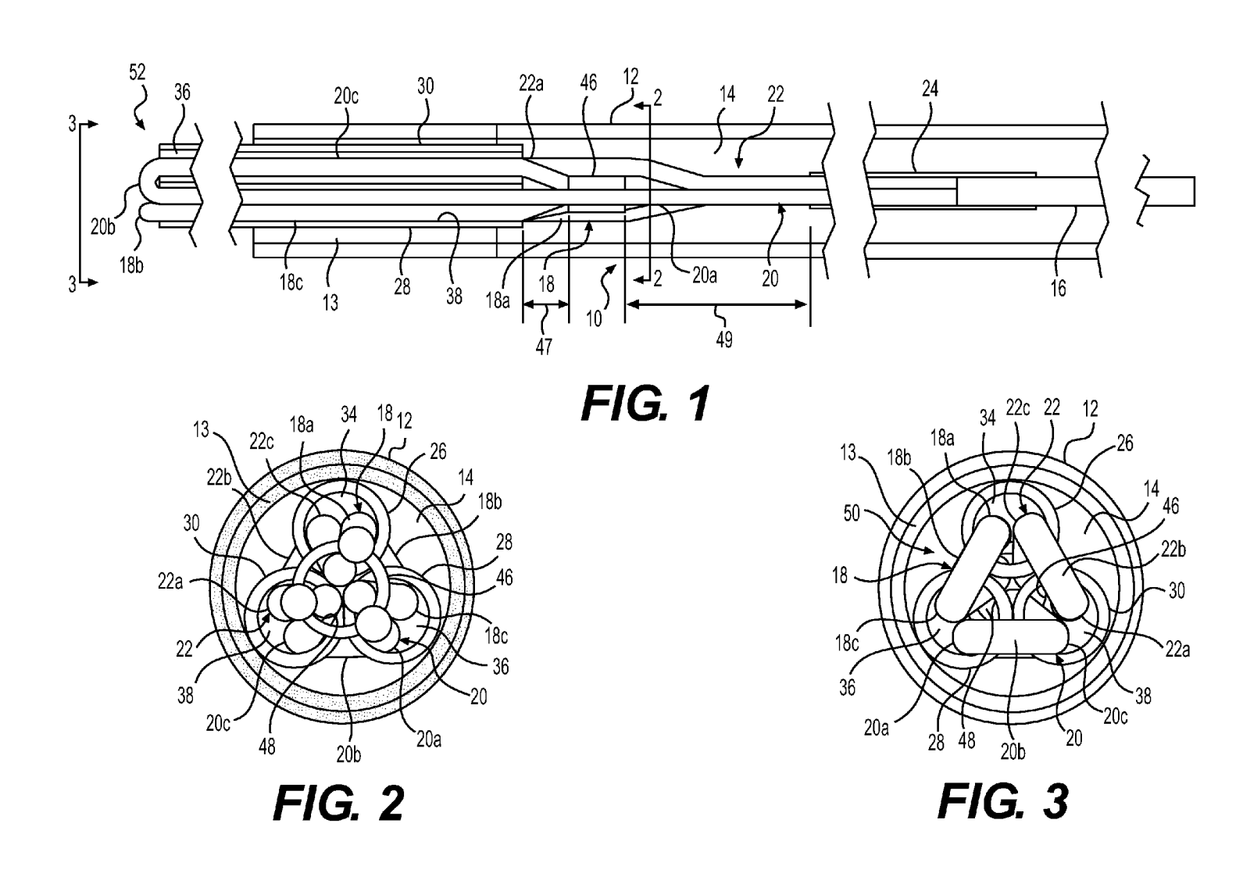
FIG. 1 is a side and partial view of a retrieval device including an end effector in a retracted and contracted state, in accordance with examples of the present disclosure.
FIG. 2 is a cross-sectional view of the retrieval device of FIG. 1, in accordance with examples of the present disclosure.
FIG. 3 is a distal end view of the retrieval device of FIG. 1, in accordance with examples of the present disclosure.
Figure 4:
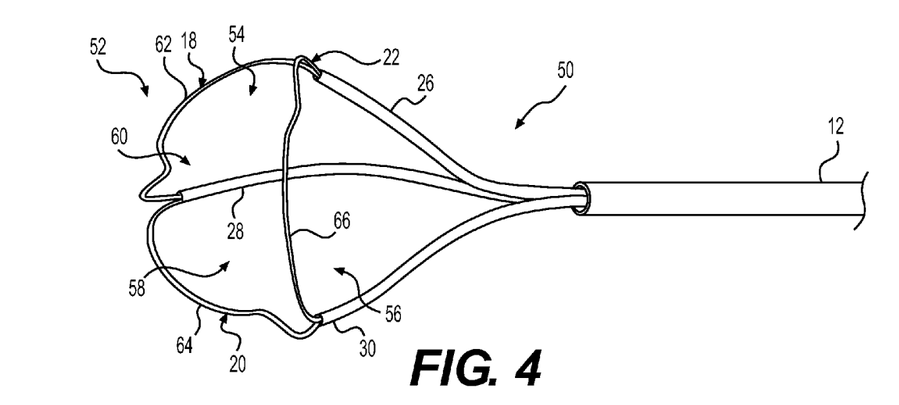
FIG. 4 is a perspective view of the retrieval device of FIG. 1 in an extended and expanded state, in accordance with examples of the present disclosure.
Figure 5:
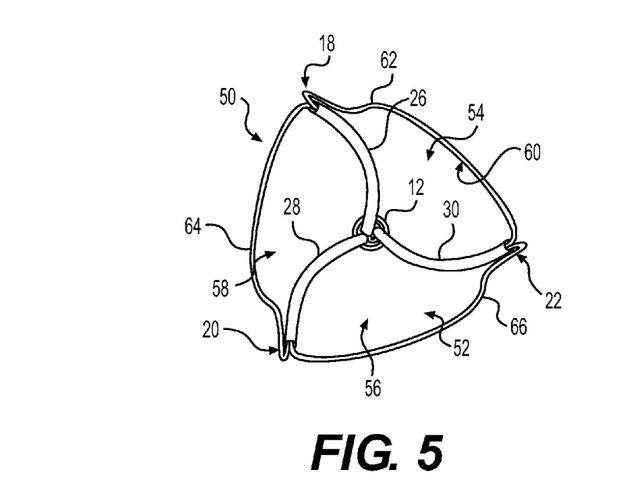
FIG. 5 is a distal end view of the retrieval device of FIG. 1 in the extended and expanded state, in accordance with examples of the present disclosure.
Figure 6:
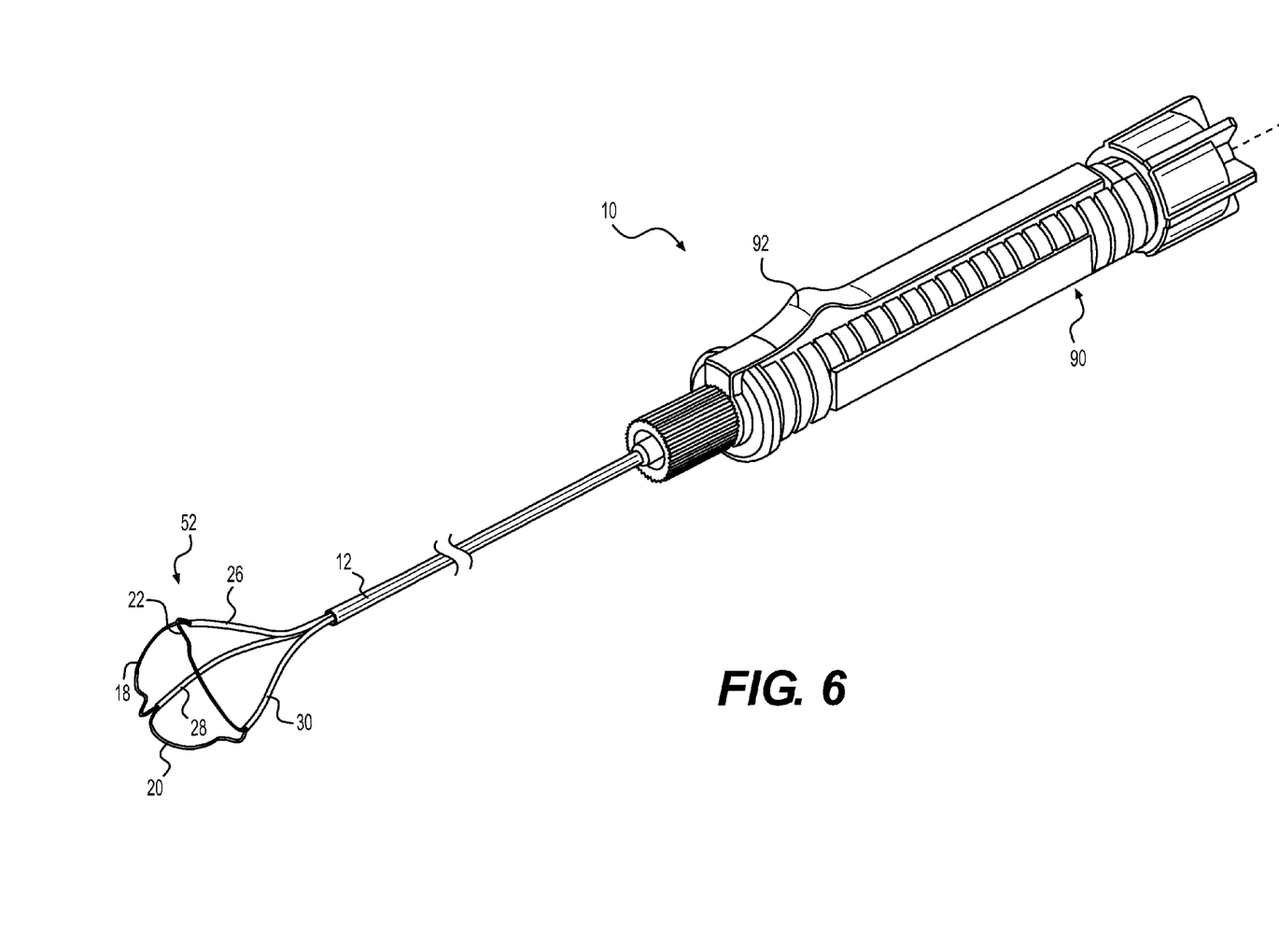
FIG. 6 is a full view of the retrieval device of FIG. 1 in the extended and expanded state.

FIGS. 1-5 show portions of a retrieval device 10, and FIG. 6 shown a full view of the device 10. Referring briefly to FIG. 6, the device 10 includes a basket portion or grasper portion 52 including a plurality of movable members 18, 20, and 22, and a plurality of support members 26, 28, and 30. The support members 26, 28, and 30 may be coupled to an outer sheath 12 and back to a handle assembly 90. The movable members may be coupled back to the handle assembly 90 through the support members 26, 28, and 30 and the outer sheath 12. As explained in more detail below, movement of an actuator 92 of the handle assembly 90 may provide relative movement between the movable members 26, 28, and 30 and support members 26, 28, and 30 to transition the grasper portion 52 between an expanded state (FIG. 6) and a contracted state (FIG. 1).

Referring to FIG. 1, the outer sheath 12 of retrieval device 10 may include a lumen 14 extending longitudinally therethrough. The outer sheath 12 may be, for example, a hollow tube of about 1.9 French, although the dimensions may differ based on the type of procedure being performed with the retrieval device 10. The outer sheath 12 may be made of a polymer material or combination of materials. A proximal portion of the outer sheath 12 may be made of a different material than a distal portion of the outer sheath 12. For example, the distal portion of the outer sheath 12 may be made of a material that is more flexible than the material of the proximal portion of the outer sheath 12.

The retrieval device 10 may also include a drive member or shaft 16. The drive member 16 may extend through the lumen 14 of the outer sheath 12. The drive member 16 may be elongated, and may include, for example, a wire, braid, cable, shaft, and/or any other suitable drive member configured to receive or transfer compression, tension, and/or torsional forces. The drive member 16 may have any suitable cross-sectional shape, including cylindrical, elliptical, polygonal, and/or irregular. The drive member 16 may be made of metals, polymers, or a combination of materials. It is also contemplated that the drive member 16 may have a diameter of approximately 0.0125 inches. The drive member 16 may have other diameters, however, depending on the type of procedure being performed with the retrieval device 10.

The movable members of retrieval device 10 may include a first movable member 18, a second movable member 20, and a third movable member 22. The first movable member 18 may include a first leg 18a, a reverse or U-shaped bend 18b, and a second leg 18c. Similarly, the second movable member 20 may include a first leg 20a, a reverse or U-shaped bend 20b, and a second leg 20c. The third movable member 22 may also include a first leg 22a, a reverse or U-shaped bend 22b, and a second leg 22c. While three movable members 18, 20, and 22 are shown, one or more additional movable members may also be included.

Each of the movable members 18, 20, and 22 may be formed of any suitable material including, but not limited to, metals, polymers, or a combination of materials. For example, one or more of the movable members 18, 20, and 22 may be formed with a shape memory material, such as Nitinol, and may be treated to possess an internal bias causing one or more of the movable members 18, 20, and 22 to move to a preselected position in the absence of an urging force. For example, the U-shaped bends 18b, 20b, 22b of the movable members 18, 20, and 22 may preformed such as by heat setting into the U-shaped bend shape. This preformed U-shaped bend 18b, 20b, 22b facilitate a clamping of the distal ends of the support members together in the contracted state (FIG. 1). One or more of the movable members 18, 20, and 22 may be a wire, braid, cable, or shaft having any suitable diameter, such as a diameter of about 0.003 inches, although other suitable diameters may alternatively be utilized.

Each of the movable members 18, 20, and 22 may have any suitable cross-sectional shape, including cylindrical, elliptical, polygonal, and/or irregular. One or more of the movable members 18, 20, and 22 may include a portion flattened, machined, extruded, drawn, and/or etched into a different profile than a remaining portion. One or more of the movable members 18, 20, and 22 may be slotted to allow deflection or directional bending. The exterior surfaces of one or more of the movable members 18, 20, and 22 may be roughened, notched, slotted, etched, sand-blasted, or otherwise modified to provide a better gripping surface.

The movable members 18, 20, and 22 may be attached to the drive member 16 at a first end. For example, proximal ends of the first legs 18*a*, 20*a*, and 22*a* may be attached to the distal end of the drive member 16. The attachment may be provided by one or more of a splice joint, adhesives, melting, welding, crimping, and/or any other suitable attachment mechanism. It is also contemplated that a sleeve 24 may be placed over the proximal portions of the first legs 18*a*, 20*a*, and 22*a*, and the distal portion of the drive member 16 to secure the elements together. The sleeve 24 may be made of a polytetrafluoroethylene like TEFLON. The sleeve 24 may be heat shrinkable onto the first legs 18*a*, 20*a*, and 22*a*, and the drive member 16. The sleeve 24 may have a length of about 11.5 cm, but it should be understood that the length and other sleeve dimensions may vary based on the type of procedure being performed with the retrieval device 10. The sleeve 24 may help gather the first legs 18*a*, 20*a*, and 22*a*, to avoid radially outwardly movement of the legs when pushed distally by the drive member 16, giving the gathered portions added strength. The proximal portions of each of the first legs 18*a*, 20*a*, and 22*a* may contact the proximal portions of the other first legs. Longitudinal axes of the proximal portions of the first legs 18*a*, 20*a*, and 22*a* may be substantially parallel.

The support members of the retrieval device 10 may include a first support member 26, a second support member 28, and a third support member 30. The support members 26, 28, and 30 may include lumens 34, 36, and 38 extending longitudinally therethrough, respectively. In one example, at least one of the support members 26, 28, and 30 may be a tube. The support members 26, 28, and 30 may be disposed circumferentially about the longitudinal axis of the outer sheath 12. The longitudinal axes of the support members may be disposed at equal intervals circumferentially about the longitudinal axis. It should, however, be noted that any other suitable number of support members and spacing configurations may alternatively be utilized. Each of the support members 26, 28, and 30 may have any suitable cross-sectional shape, including cylindrical elliptical, polygonal, and/or irregular. One or more of the support members 26, 28, and 30 may include a portion flattened, machined, extruded, drawn, and/or etched into a different profile than a remaining portion. One or more of the support members 26, 28, and 30 may be slotted to allow deflection or directional bending. One or more of the support members 26, 28, and 30 may have an inner diameter of about 0.007 inches, a wall thickness of about 0.001 inches, and/or a length of about 19.5 millimeters, although other suitable dimensions may alternatively be utilized. The exterior surfaces of one or more of the support members 26, 28, and 30 may be roughened, notched, slotted, etched, sand-blasted, or otherwise modified to provide a better gripping surface. The support members 26, 28, and 30 may be made of coaxial tubes or heat shrink tubes, and made of any suitable material or combination of materials, including a polymer such as polyimide, or polyethylene terephthalate.

As shown in FIG. 1, the movable members 18, 20, and 22 may be extend distally from the first, proximal end that is coupled to the drive member 16, extend distally through a support member 26, 28, and 30 along the first leg 18*a*, 20*a*, and 22*a*, form the preformed U-shaped bend 18*b*, 20*b*, and 22*b*, and extend proximally through a different support member 26, 28, and 30 along the second leg 18*c*, 20*c*, and 22*c*. In this configuration, the preformed U-shaped bend may confine or urge the support members 26, 28, and 30 toward a low profile in the contracted state.

The movable members 18, 20, and 22, and the support members 26, 28, and 30, may be heat treated simultaneously, and the material for the movable members 18, 20, and 22 and the support members 26, 28, and 30 may be selected such that the support members 26, 28, and 30 will not melt during heat treatment of the movable members 18, 20, and 22. While three support members 26, 28, and 30 are shown, one or more additional support members may be used.

Proximal portions of the support members 26, 28, and 30 may extend through the lumen 14, and may be covered by the outer sheath 12. For example, a length of about 10 millimeters of one or more of the support members 26, 28, and 30 may be covered by the outer sheath 12, leaving a length of about 9.5 millimeters exposed distal to the outer sheath 12. Each of the support members 26, 28, and 30 may contact the other two support members. For example, each of the proximal portions of the support members 26, 28, and 30 may contact the proximal portions of the other two support members, such that the support members 26, 28, and 30 may have a triangular arrangement around the longitudinal axis of the outer sheath 12, as shown in FIGS. 2 and 3. Longitudinal axes of the support members 26, 28, and 30 may form vertices of a triangle, and portions of the longitudinal axes may be parallel.

Distal portions of the support members 26, 28, and 30 may extend distally out of the lumen 14 and away from the distal end of the outer sheath 12. The distal portions may be configured to move towards and away from the longitudinal axis of the outer sheath 12. The number of support members 26, 28, and 30 may be equal to the number of movable members 18, 20, and 22. Alternatively, the number of support members 26, 28, and 30 may be less than the movable members 18, 20, and 22. For example, a single movable member may form two of the movable members 18, 20, and 22, for use with three support members.

Each of the three support members 26, 28, and 30 may be coupled to the outer sheath 12. For example, proximal ends of the support members 26, 28, and 30 that are covered by the distal end of the outer sheath 12 may be fixedly coupled to the distal end of the outer sheath 12 by an adhesive 13, such as an ultraviolet light curable adhesive or cyanoacrylate. Additionally or alternatively, the distal end of the outer sheath 12 may be fixedly coupled to the proximal ends of the support members 26, 28, and 30 by heat shrinking or by using a coupling tube glued at both ends. The coupling may keep the proximal ends of the support members 26, 28, and 30 stationary relative to the distal end of outer sheath 12, while allowing the distal ends of the support members 26, 28, and 30 to move relative to the distal end of the outer sheath 12 and relative to one another.

The first leg 18*a* may extend distally from the drive member 16, and may enter the lumen 34 at the proximal end of the first support member 26. The first leg 18*a* may extend distally through the lumen 34, and may exit the lumen 34 at the distal end of the first support member 26. There the first leg 18*a* may transition into the bend 18*b*. The bend 18*b* may transition into the second leg 18*c*. The second leg 18*c* may enter the lumen 36 at the distal end of the second support member 28. The second leg 18*c* may extend proximally through the lumen 36, and may exit the lumen 36 at the proximal end of the second support member 28.

The first leg 20*a* may extend distally from the drive member 16, and may enter the lumen 36 at the proximal end of the second support member 28. The first leg 20*a* may extend distally through the lumen 36, and may exit the lumen 36 at the distal end of the second support member 28. There the first leg 20a may transition into the bend 20b. The bend 20b may transition into the second leg 20c. The second leg 20c may enter the lumen 38 at the distal end of the third support member 30. The second leg 20c may extend proximally through the lumen 38, and may exit the lumen 38 at the proximal end of the third support member 30.

The first leg 22a may extend distally from the drive member 16, and may enter the lumen 38 at the proximal end of the third support member 30. The first leg 22a may extend distally through the lumen 38, and may exit the lumen 38 at the distal end of the third support member 30. There the first leg 22a may transition into the bend 22b. The bend 22b may transition into the second leg 22c. The second leg 22c may enter the lumen 34 at the distal end of the first support member 26. The second leg 22c may extend proximally through the lumen 34, and may exit the lumen 34 at the proximal end of the first support member 26.

Alternatively, it is contemplated that the first leg 18a may extend distally through the first support member 26, and the second leg 18c may extend proximally through the third support member 30. The first leg 20a may extend distally through the second support member 28, and the second leg 20c may extend proximally through the first support member 26. The first leg 22a may extend distally through the third support member 30, and the second leg 22c may extend proximally through the second support member 28.

One or more of the proximal or second ends of the second legs 18c, 20c, and 22c may include a movable stop sized to abut or engage a proximal end of a support member 26, 28, and 30 after moving a distance 47 distally during movement of the retrieval device toward the expanded state. The movable stop may be formed in a number of different ways. An exemplary movable stop is shown in FIG. 1 and includes a coupler 46 in the form of a tube including a lumen 48 configured to receive proximal ends of the second legs 18c, 20c, and 22c. The second legs 18c, 20c, and 22c may be attached to each other within the coupler 46 and attached to the coupler 46. For example, each of the second legs 18c, 20c, and 22c may be attached to each other and the coupler 46 by adhesive, melting, welding, crimping, friction fit, heat-shrinking the coupler 46, and/or any other suitable form of attachment. Portions of the first legs 18a, 20a, and 22a may extend along the side of the coupler 46, and may contact the exterior surface of the coupler 46. The coupler 46 may space portions of the first legs 18a, 20a, and 22a apart from the longitudinal axis of the outer sheath 12, to help guide the first legs 18a, 20a, and 22a into the support members 26, 28, and 30.

Alternatively, the movable stop could be formed by replacing the two movable members 18 and 20 with a single moveable member having a U-shaped bend replacing the proximal ends of the second legs 18c and 20c. In this arrangement, the U-shaped bend could form the movable stop of the movable members against the proximal end of the support members 26, 28, and 30 during a first phase of the expansion of the retrieval device 10. Further, the second leg 22c could be coupled to the U-shaped bend to limit its travel. Alternatively, proximal U-shaped or L-shaped hooks, or any other type of obstruction (not shown) could be provided on one, two, or all of the second legs 18c, 20c, and 22c to form the movable stop for abutting or engaging the support members 26, 28, and 30 and limiting movement of the second legs 18c, 20c, and 22c to the distance 47 during the first phase of expansion of the retrieval device 10.

The movable members 18, 20, and 22, and the support members 26, 28, and 30, may form an end effector 50. The end effector 50 may together form the basket or grasper portion 52. In FIGS. 1-3, the grasper portion 52 is shown in the retracted and contracted state. The grasper portion 52 may be moved into its retracted and contracted state by moving the drive member 16 proximally relative to the outer sheath 12, or moving the sheath 12 distally relative to the drive member 16. Reference to "movable" members 26, 28, 30 refers to the relative movement of members 26, 28, 30 in relation to other elements of the device 10, and thus it is understood that the term "movable" in movable members 26, 28, and 30 includes the members being stationary during movement between the contracted and expanded states, but movable in relation to support members 26, 28, and 30 during movement between the contracted and expanded states. In the retracted/contracted state, the bends 18b, 20b, and 22b may be at or adjacent to the distal ends of the support members 26, 28, and 30. Distal ends of the first legs 18a, 20a, and 22a and the second legs 18c, 20c, and 22c may be positioned within the lumens 34, 36, and 38 of the support members 26, 28, and 30. The longitudinal axes of the support members 26, 28, and 30 may be substantially parallel, and both proximal and distal portions of each of the support members 26, 28, and 30 may be in contact with the other support members. Portions of the first legs 18a, 20a, and 22a and the second legs 18c, 20c, and 22c in the lumens 34, 36, and 38 may be substantially parallel. The support members 26, 28, and 30, and/or the outer sheath 12 may help to resist bowing of the movable members 18, 20, and 22 during movement of the device between the expanded and contracted states.

In the retracted/contracted state, the distal end of the coupler 46 may be spaced from the proximal ends of the support members 26, 28, and 30 by a distance 47. The distance 47 may be about 1 millimeter, although other distances may also be used. The proximal end of the coupler 46 may be spaced from the distal end of the sleeve 24 by a distance including a distance 49. The distances 49 may total to about 16 millimeters, although other distances may also be used. In another example, distance 49 may be about 11 millimeters. Smaller distances may position sleeve 24 in a more proximal position relative to a flexible ureteroscope channel where the ureteroscope scope does not deflect. This positioning may prevent binding of a rigid sleeve 24 within a curved portion of sheath 12. However, it is also contemplated that sleeve 24 may include one or more flexible materials. The distances 47 and 49 may vary based on the procedure being performed with the retrieval device 10.

In FIGS. 4 and 5, the retrieval device 10 is shown with the grasper portion 52 in an extended and expanded state. In the extended and expanded state, portions of the movable members 18, 20, and 22 may be exposed from the distal ends of the support members 26, 28, and 30 and the outer sheath 12. Once exposed, one or more of the movable members 18, 20, and 22 may move radially outwardly from the longitudinal axis of the outer sheath 12 due to a natural and/or applied radially outward biasing in one or more of the movable members 18, 20, and 22. Radially outward movement of one or more of the movable members 18, 20, and 22 may cause a corresponding radially outward movement of the support members 26, 28, and 30.

The exposed portions of the movable members 18, 20, and 22 may form bridges 62, 64, and 66 between the distal ends of the support members 26, 28, and 30. Each bridge may extend distally from the distal end of a given support member, and may be received in the distal end of an adjacent support member. The bridges 62, 64, and 66 may be formed by distal portions of the first legs 18a, 20a, and 22a, the bends 18b, 20b, and 22b, and distal portions of the second legs 18c, 20c and 22c.

Each bridge and its corresponding two support members may form a side loop of the grasper portion 52. Three side loops 54, 56, and 58 are shown in FIGS. 4 and 5. The bridges 62, 64, and 66 may form a front loop 60 of the grasper portion 52. Materials may enter the grasper portion 52 through one or more of the front loop 60 and the side loops 54, 56, and 58. By adding additional movable members and support members, additional side loops can be created.

Relative movement between drive member 16 and outer sheath 12 causes grasper portion 52 to move to its extended and expanded state due to a natural and/or applied radially outward biasing in one or more of the movable members 18, 20, and 22. Extension and expansion of the grasper portion 52 may occur in phases. Starting from the retracted and contracted state shown in FIG. 1, a first phase of the extension and expansion of the grasper portion 52 may begin with movement of the drive member 16 distally relative to the outer sheath 12 and the support members 26, 28, and 30. The relative movement of the drive member 16 may cause the movable members 18, 20, and 22 and the coupler 46 to move distally relative to the outer sheath 12. The movement of the drive member 16, movable members 18, 20, and 22, and coupler 46 may be translational. For example, the drive member 16, first legs 18a, 20a, and 22a, bends 18b, 20b, and 22b, second legs 18c, 20c, and 22c, and coupler 46, may move distally relative to the outer sheath 12 and support members 26, 28, and 30 during the first phase. Proximal portions of the first legs 18a, 20a, and 22a and second legs 18c, 20c, and 22c may enter the lumens 34, 36, and 38 of the support members 26, 28, and 30 at the proximal ends of the support members 26, 28, and 30. Distal portions of the first legs 18a, 20a, and 22a, bends 18b, 20b, and 22b, and second legs 18c, 20c, and 22c may emerge from, or extend further out from, the distal ends of the support members 26, 28, and 30.

The coupler 46 forming the movable stop moves with the movable members 18, 20, and 22 relative to the outer sheath 12 and support members 26, 28, and 30. When the coupler 46 has traveled the distance 47 relative to the outer sheath 12 and support members 26, 28, and 30, further distal movement of the coupler 46 may be halted as the coupler 46 approaches the proximal ends of the support members 26, 28, and 30. This prevents the second legs 18c, 20c, and 22c from further entering the lumens 34, 36, and 38 of the support members 26, 28, and 30. At the end of the first phase of extension and expansion, the bends 18b, 20b, and 22b may each be spaced from distal ends of the support members 26, 28, and 30 by the distance 47 because the U-shaped bends 18b, 20b, and 22b are located a fixed distance from the coupler 46.

The presence of distance 47 between the support members 26, 28, and 30, and the coupler 46 facilitates the reciprocal movement of retrieval device 10 between the contracted and expanded states. That is, the presence of distance 47 reduces an initial amount of force required to move retrieval device 10 from the contracted state toward the expanded state. As described above, movable members 18, 20, and 22 may include a preset U-shape bend 18b, 20b, and 22b that serves to help clamp the distal end of the support members 26, 28, and 30 in the contracted state. By extending the movable members 18, 20, and 22 the distance 47, the clamping resistance of the U-shaped bends 18b, 20b, and 22b on the distal ends of the support members 26, 28, and 30 is reduced. Moreover, movement of the movable members 18, 20, and 22 away from the distal end of the support members 26, 28, and 30 provides a greater moment arm to overcome the bias of the U-shaped bends 18b, 20b, and 22b when moving the retrieval device 10 toward the expanded state.

The presence of distance 47 may also permit retrieval device 10 to form a first stage grasper by the portion of the movable members 18, 20, and 22 extending distally of the support members 26, 28, and 30. This first stage grasper can capture smaller fragments within only the portion of movable members 18, 20, and 22 extending distally from support members 26, 28, and 30 after movement of the distance 47. The distal ends of movable members 18, 20, and 22 may more securely capture smaller fragments than support members 26, 28, and 30 because they include a more distributed contact array or wire web than the support members 26, 28, and 30. It is noted that during the first phase movement of the movable members 18, 20, and 22, the support members extend generally parallel to one another. As understood, the word "generally" as used herein means mainly, and if more specificity is required, means a range of plus or minus eight percent of the relevant value.

A second phase of the extension and expansion of the grasper portion 52 may begin after distal movement of the coupler 46 has been halted. During the second phase, further distal movement of the drive member 16 relative to the outer sheath 12 and support members 26, 28, and 30 may drive distal movement of the first legs 18a, 20a, and 22a relative to the outer sheath 12 and support members 26, 28, and 30. During the second phase, the second legs 18c, 20c, and 22c may remain stationary relative to the support members 26, 28, and 30. The first legs 18a, 20a, and 22a may be increasingly exposed from the distal ends of the support members 26, 28, and 30, thereby increasing the lengths of the bridges 62, 64, and 66. Distal portions of the movable members 18, 20, and 22, and the support members 26, 28, and 30, may expand radially outwardly. The front loop 60 and the side loops 54, 56, and 58 may also expand in size.

Extension and expansion in the second phase may continue over the distance 49. Once the first legs 18a, 20a, and 22a have traveled the distance 49, distal movement of the drive member 16 may halt. Distal movement of the drive member 16 may be halted, for example, by a stop formed in the handle assembly described in FIG. 6.

Moving the grasper portion 52 back to the retracted and contracted state may be accomplished by moving the drive member 16 proximally relative to the outer sheath 12 and support members 26, 28, and 30. Movement from the extended and expanded state to the retracted and contracted state may also occur in phases. A first phase of the retraction and contraction of the grasper portion 52 may begin with the drive member 16 moving proximally relative to the outer sheath 12. This may cause the first legs 18a, 20a, and 22a to move proximally relative to the outer sheath 12 and support members 26, 28, and 30. Distal portions of the first legs 18a, 20a, and 22a may enter the lumens 34, 36, and 38 at the distal ends of the support members 26, 28 and 30. The second legs 18c, 20c, and 22c, and the coupler 46 may remain stationary relative to the support members 26, 28, and 30. The lengths of the bridges 62, 64, and 66 may decrease. The first legs 18a, 20a, and 22a, second legs 18c, 20c, and 22c, and support members 26, 28, and 30 may move radially inwardly. Thus, the front loop 60 and the side loops 54, 56, and 58 may decrease in size.

The first phase of the retraction and contraction of the grasper portion 52 may take place over the distance 49. Once the distance 49 has been covered, a second phase of the retraction and contraction may take place with continued movement of the drive member 16 proximally relative to the outer sheath 12 and the support members 26, 28, and 30. The continued movement may cause the movable members 18, 20, and 22 and the coupler 46 to move distally relative to the outer sheath 12 and support members 26, 28, and 30. The movement of the drive member 16, movable members 18, 20, and 22, and coupler 46 may be translational. For example, the drive member 16, first legs 18a, 20a, and 22a, bends 18b, 20b, and 22b, second legs 18c, 20c, and 22c, and coupler 46, may move proximally relative to the outer sheath 12 and support members 26, 28, and 30 during the second phase. Proximal portions of the first legs 18a, 20a, and 22a and second legs 18c, 20c, and 22c may exit the lumens 34, 36, and 38 of the support members 26, 28, and 30 at the proximal ends of the support members 26, 28, and 30. Distal portions of the first legs 18a, 20a, and 22a, bends 18b, 20b, and 22b, and second legs 18c, 20c, and 22c may enter into, or move further past, the distal ends of the support members 26, 28, and 30. The lengths of the bridges 62, 64, and 66 may decrease as the exposed lengths of the movable members 18, 20, and 22 decrease. As the bridges 62, 64, and 66 shrink, distal portions of the movable members 18, 20, and 22, and the support members 26, 28, and 30, may contract radially inwardly toward the longitudinal axis of the outer sheath 22. The front loop 60 and side loops 54, 56, and 58 may also shrink in size.

The coupler 46 may move with the movable members 18, 20, and 22 relative to the outer sheath 12 and support members 26, 28, and 30. When the coupler 46 has traveled the distance 47 relative to the outer sheath 12 and support members 26, 28, and 30, further proximal movement of the coupler 46 may be halted by operation of the handle assembly 90, such as a stop formed in the handle assembly 90 of FIG. 6. At the end of the second phase of retraction and contraction, the state shown in FIG. 1 is attained. As noted above, in this contracted state, movable members 18, 20, and 22 may include preset U-shape bends 18b, 20b, and 22b located adjacent the distal ends of the support members 26, 28, and 30 that serve to help clamp the distal end of the support members 26, 28, and 30 in the contracted state.

FIG. 6 illustrates the handle assembly 90 disposed at the proximal end 86 of the retrieval device 10. Handle assembly 90 may include an actuator 92 such as, e.g., a sliding mechanism, rotating mechanism, pushing mechanism, or the like. Actuator 92 may be coupled to outer sheath 12 and include internal stops for limiting movement of the outer sheath 12 relative to the movable members 18, 20, and 22. The drive member 16 may be fixed to a proximal end of the handle assembly 90. It is understood that the handle assembly may be formed in any conventional manner to control the movement of movable members 18, 20, and 22 relative to the outer sheath 12 and support members 26, 28, and 30 as described above. As noted above, handle assembly 90 may include one or more internal or external stops to limit movement of the movable members 18, 20, and 22.

Figure 7:
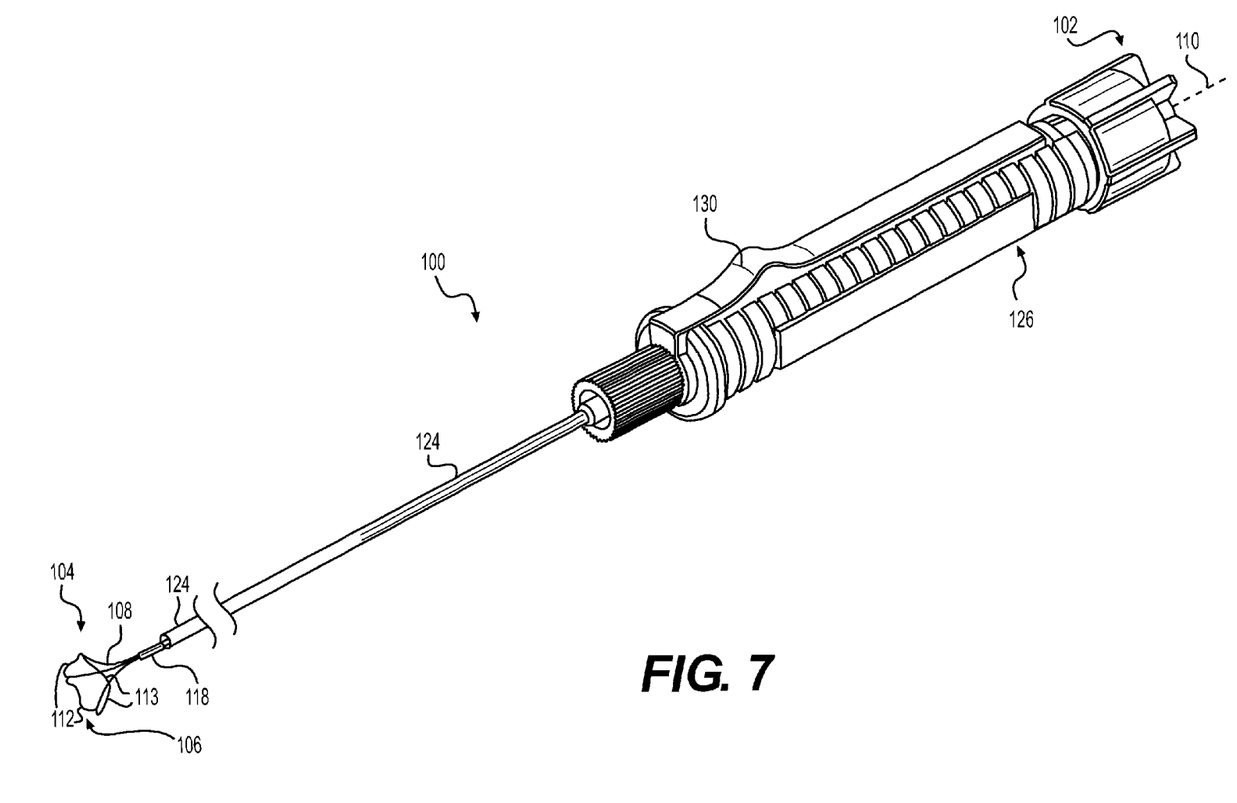
FIG. 7 is a perspective view of a medical retrieval device with a basket in an expanded configuration in accordance with an example of the present disclosure.
Figure 8:
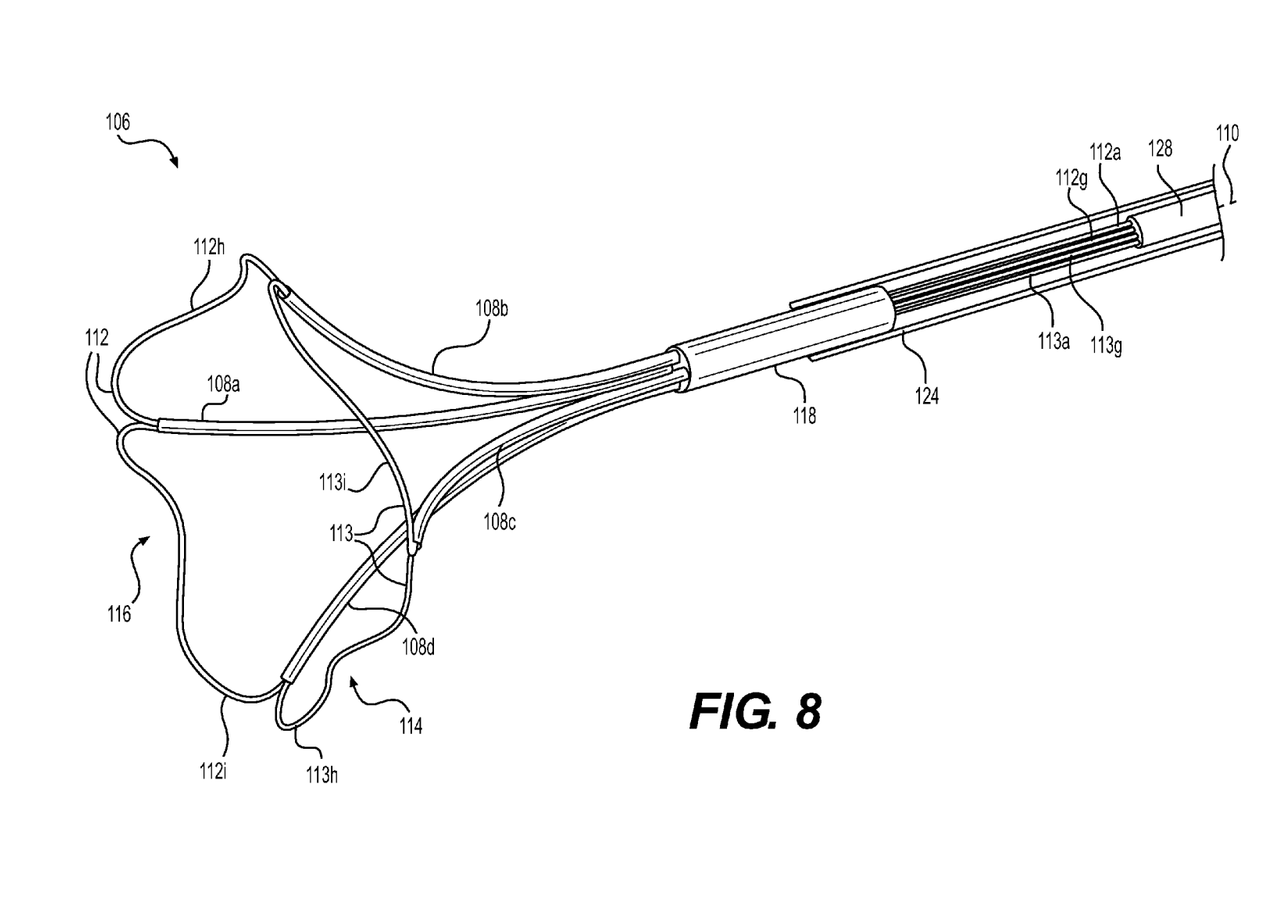
FIG. 8 is an enlarged partial perspective view of the basket of the medical device of FIG. 7.

As shown in FIGS. 7 and 8, a medical device 100 according to an example of the present disclosure may extend from a proximal end 102 toward a distal end 104. Medical device 100 may include a handle 126 disposed at proximal end 102. Handle 126 may include an actuator 130 such as, e.g., a sliding mechanism, rotating mechanism, pushing mechanism, or the like. Actuator 130 may be coupled to a drive member 128 (shown only in FIG. 8) in any conventional manner to control the movement of a basket 106 disposed at distal end 104 of medical device 100. Drive member 128 may be a filament, braided wire, rope, rod, or other suitable drive member.

Figure 9:
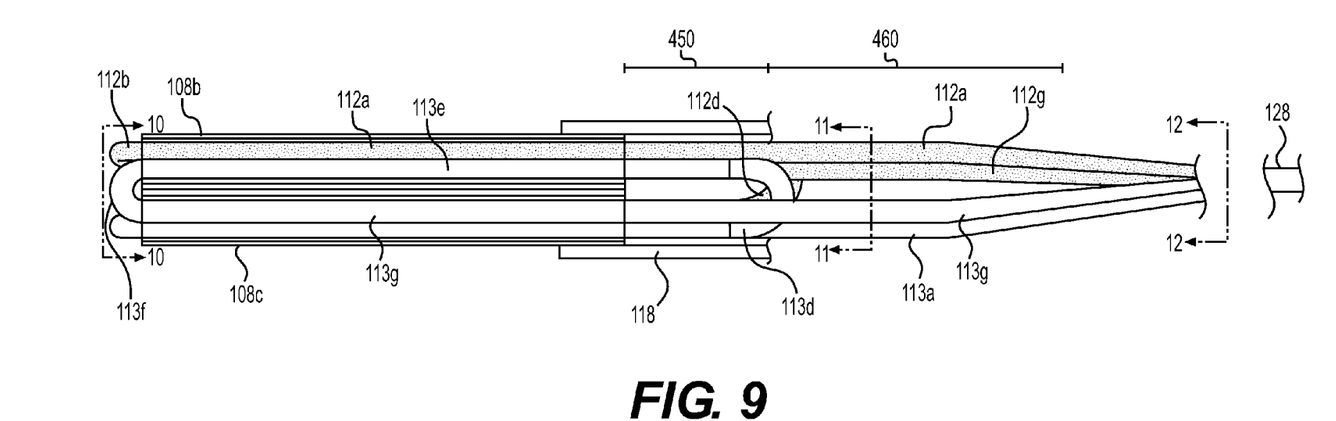
FIG. 9 is an enlarged partial side and cross-sectional view of the medical retrieval device of FIG. 7.
Figure 10:
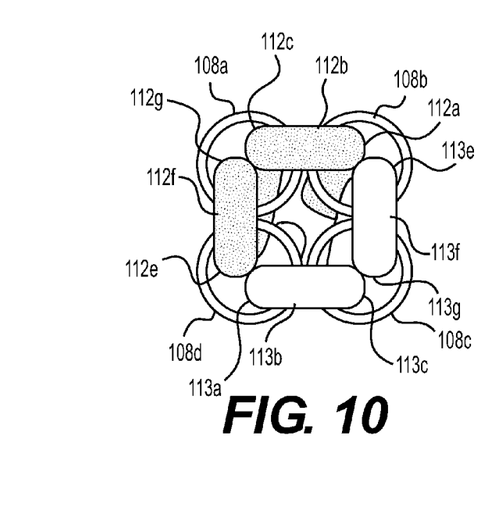
FIG. 10 is a top view of the medical retrieval device of taken along line 10-10 of FIG. 9.
Figures 11, 12:
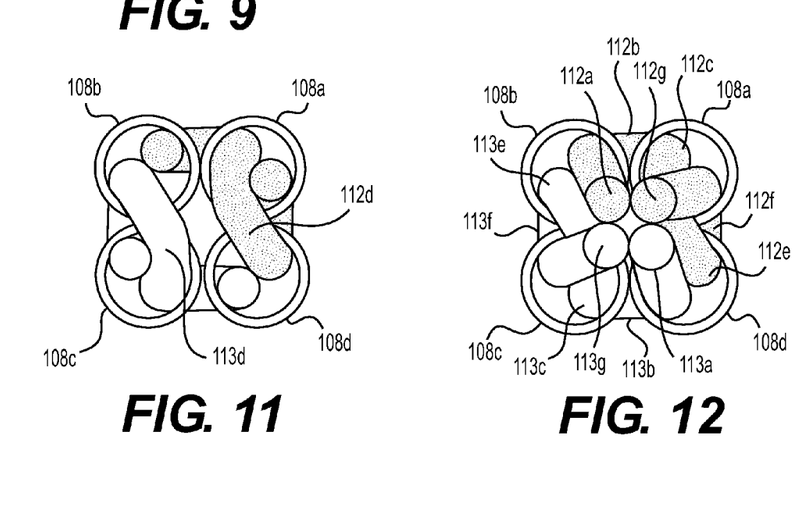
FIG. 11 is a cross-sectional view of the medical retrieval device taken along line 11-11 of FIG. 9.
FIG. 12 is a cross-sectional view of the medical retrieval device taken along line 12-12 of FIG. 9.
Figure 13:
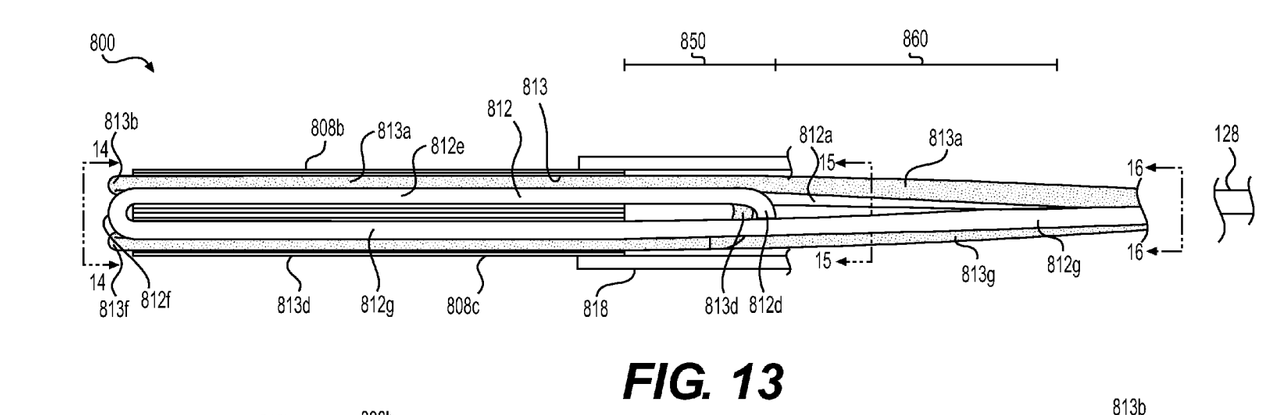
FIG. 13 is an enlarged partial side and cross-sectional view of a medical retrieval device in accordance with another example of the present disclosure.
Figure 14:
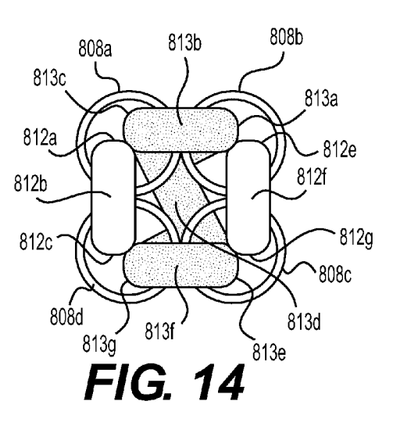
FIG. 14 is a top view of the medical retrieval device taken along line 14-14 of FIG. 13.
Figure 15:
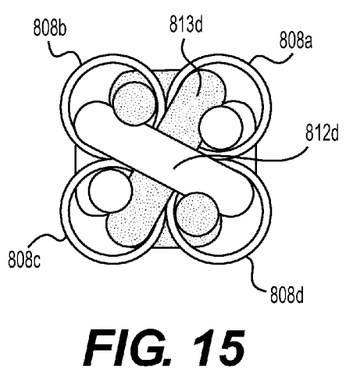
FIG. 15 is a cross-sectional view of the medical retrieval device taken along line 15-15 of FIG. 13.
Figure 16:
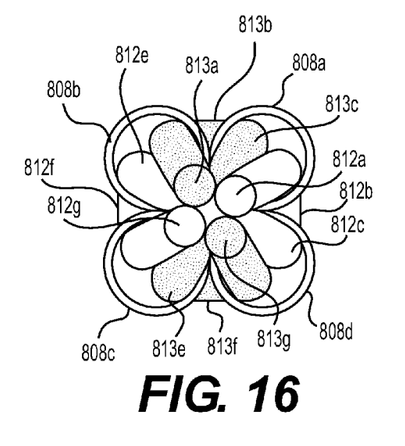
FIG. 16 is a cross-sectional view of the medical retrieval device taken along line 16-16 of FIG. 13.

Basket 106 may include a plurality of branch members 108 and movable members 112 and 113 passing through the branch members 108 as will be explained in more detail below. Basket 106 may be configured to reciprocally move between an expanded configuration (shown in FIGS. 7 and 8) and a collapsed configuration (shown in FIGS. 9-12). A sheath 118 (shown in FIGS. 8 and 9) may be fixedly disposed around the proximal ends of branch members 108. Distal portions of the branch members 108 may extend distally out of the sheath 118. The distal portions of branch members 108 may be configured to move towards and away from the longitudinal axis of the sheath 118. In some examples, sheath 118 may extend proximally to encompass at least a portion of movable members 112, 113. The proximal end of sheath 118 may be coupled to a strain relief portion 124. Strain relief portion 124 may be configured to provide support between handle 126 and a proximal end of sheath 118. Thus, the proximal ends of sheath 118 and strain relief portion 124 may be coupled to handle 126.

Each of the movable members 112, 113 may have any suitable cross-sectional shape, including cylindrical, elliptical, polygonal, and/or irregular. One or more of the movable members 112, 113 may include a portion flattened, machined, extruded, drawn, and/or etched into a different profile than a remaining portion. One or more of the movable members 112, 113 may be slotted to allow deflection or directional bending. The exterior surfaces of one or more of the movable members 112, 113 may be roughened, notched, slotted, etched, sand-blasted, or otherwise modified to provide a better gripping surface. One or more of the movable members 112, 113 may be formed of any suitable material including, but not limited to, metals, polymers, or a combination of materials. In one example, one or more of the movable members 112, 113 may include a metal wire coated with a polymer. In an alternative example, one or more of the movable members 112, 113 may be formed from two or more metals that are co-drawn together. In one example, one or more of the movable members 112, 113 may be formed with a shape memory material, such as, e.g., Nitinol wires having a diameter of about 0.003".

The movable members 112, 113 may be attached to the drive member 128. For example, proximal ends of a first leg 112a, a fourth leg 112g, a first leg 113a, and a fourth leg 113g may be attached to the distal end of the drive member 128. The attachment may be provided by one or more of a splice joint, adhesives, melting, welding, crimping, and/or any other suitable attachment mechanism.

Referring to FIG. 8, the longitudinal axes of the branch members 108 may be disposed at equal intervals circumferentially about longitudinal axis 110. It should, however, be noted that any other suitable number of branch members and spacing configurations may alternatively be utilized. In some examples, branch members 108 may be hollow tubes configured to receive the movable members 112, 113 therethrough. In some examples, the proximal ends of branch members 108 may be coupled to one another. Each of the branch members 108 may have any suitable cross-sectional shape, including cylindrical, elliptical, polygonal, and/or irregular. One or more of the branch members 108 may include a portion flattened, machined, extruded, drawn, and/or etched into a different profile than a remaining portion. One or more of the branch members 108 may be slotted to facilitate deflection or directional bending. One or more of the branch members 108 may have an inner diameter of about 0.007 inches, a wall thickness of about 0.001 inches, and/or a length of about 19.5 millimeters, although other suitable dimensions may alternatively be utilized. The exterior surfaces of one or more of the branch members 108 may be roughened, notched, slotted, etched, sand-blasted, or otherwise modified to provide a better gripping surface. The branch members 108 may be made of any suitable material, including a polymer such as polyimide, or polyethylene terephthalate.

In some examples, branch members 108 and/or movable members 112, 113 may be biased (e.g., pre-bent or curved) such that in the expanded configuration, branch members 108 and/or movable members 112, 113 are naturally urged radially outward from longitudinal axis 110 of medical device 100. Alternatively, branch members 108 and/or movable members 112, 113 may be unbiased, in that their neutral position is straight and parallel with the longitudinal axis 110 of medical device 100.

Exposed portions of the movable members 112, 113, that extend distally from a given branch member 108, may form bridges 112h, 112i, 113h, and 113i between the distal ends of the branch members 108. That is, each bridge 112h, 112i, 113h, and 113i may extend distally from the distal end of a given branch member 108, and may be received in the distal end of an adjacent branch member 108. The bridges 112h, 112i, 113h, and 113i may be formed by distal portions of first leg 112a, fourth leg 112g, first leg 113a, and fourth leg 113g, and bends 112b, 112f, 113b, and 113f (shown in FIG. 10). Materials may enter basket 106 via one of a plurality of side openings 114 defined by adjacent branch members 108, or via a distal opening 116 defined by adjacent bridges.

Branch members 108 may be secured within sheath 118 by an adhesive, such as, e.g., an ultraviolet light curable adhesive, glue, or cyanoacrylate. It should be noted, however, that any other suitable adhesive, or securing mechanism may alternatively be utilized. Sheath 118 may be formed of a polymer, such as, e.g., polyimide or polyethylene terephthalate, among others. Adhesive may be applied around the proximal ends of branch members 108 to secure them circumferentially within sheath 118. Alternatively, sheath 118 may be a heat shrink disposed around the proximal ends of branch members 108. The coupling may keep the proximal ends of the branch members 108 stationary relative to the distal end of sheath 118, while allowing the distal ends of the branch members 108 to move relative to the distal end of the sheath 118 and relative to one another.

Referring to FIGS. 9-12, first leg 112a of movable member 112 may extend distally from the drive member 128, and may enter the proximal end of a branch member 108b. The first leg 112a may extend distally through branch member 108b, and may exit the distal end of the branch member 108b. There, the first leg 112a may transition into a bend 112b. The bend 112b may transition into a second leg 112c. The second leg 112c may enter the distal end of a branch member 108a. The second leg 112c may extend proximally through branch member 108a, and may exit the proximal end of branch member 108a. There, the second leg 112c may transition into a bend 112d that encompasses a middle portion (including the midpoint) of movable member 112. Bend 112d may transition into a third leg 112e. The third leg 112e may enter the proximal end of a branch member 108d. The third leg 112e may extend distally through branch member 108d, and may exit the distal end of branch member 108d. There, third leg 112e may transition into bend 112f. Bend 112f may transition into fourth leg 112g. The fourth leg 112g may extend proximally through branch member 108a, and may exit the proximal end of branch member 108a. There, fourth leg 112g may be coupled to drive member 128.

First leg 113a of movable member 113 may extend distally from the drive member 128, and may enter the proximal end of branch member 108d. The first leg 113a may extend distally through branch member 108d, and may exit the distal end of the branch member 108d. There, the first leg 113a may transition into a bend 113b. The bend 113b may transition into a second leg 113c. The second leg 113c may enter the distal end of a branch member 108c. The second leg 113c may extend proximally through branch member 108c, and may exit the proximal end of branch member 108c. There, the second leg 113c may transition into a bend 113d that encompasses a middle portion (including the midpoint) of movable member 113. Bend 113d may transition into a third leg 113e. The third leg 113e may enter the proximal end of branch member 108b. The third leg 113e may extend distally through branch member 108b, and may exit the distal end of branch member 108b. There, third leg 113e may transition into bend 113f. Bend 113f may transition into fourth leg 113g. The fourth leg 113g may extend proximally through branch member 108c, and may exit the proximal end of branch member 108c. There, fourth leg 113g may be coupled to drive member 128.

Thus, in the example shown in FIGS. 7-12, branch members 108a and 108c may represent an alternating pair of branch members each having two legs of a respective same movable member disposed therethrough (e.g., legs 112c and 112g of movable member 112 may be disposed through branch member 108a, while legs 113c and 113g of movable member 113 may be disposed through branch member 108c). Branch members 108b and 108d may represent an alternating pair of branch members each having a portion of two different movable members disposed therethrough (e.g., leg 112a of movable member 112 and leg 113e of movable member 113 may be disposed through branch member 108b, while leg 112e of movable member 112 and leg 113a of movable member 113 may be disposed through branch member 108d).

To move medical device 100 from the collapsed configuration of FIGS. 9-12 to, e.g., the expanded configuration shown in FIGS. 7 and 8, drive member 128 (referring to FIG. 8) may be moved distally to direct movable members 112 and 113 distally. Initially, the entireties of both movable members 112 and 113 move distally and longitudinally (and with respect to branch members 108a-d) by a distance 450 (shown only in FIG. 9). The distance 450 may be determined by the distance between the proximal ends of branch members 108a-d and bends 112d and 113d. That is, the entireties of movable members 112, 113 may move longitudinally until medical device 100 reaches an intermediate configuration when bend 112d engages the proximal ends of branch members 108a and 108d, and bend 113d engages the proximal ends of branch members 108b and 108c. While bends 112d and 113d are engaged with the proximal ends of branch members 108a-d, bends 112d and 113d may have moved distally by a distance 450 such that no distance is disposed between bends 112d and 113d and the proximal ends of branch members 108a-d. As movable members 112 and 113 move distally by the distance 450, bridges 112h, 113i, 113h, and 112i (referring to FIG. 8) extend from the distal ends of branch members 108a, 108b, 108c, and 108d, respectively, by the distance 450. Once bends 112d and 113d are engaged with the proximal ends of branch members 108a-d, drive member 128 may be moved distally by an additional distance 460, displacing bridges 112h, 113i, 113h, and 112i distally by the additional distance 460. Thus, in a fully expanded configuration, bridges 112h, 113i, 113h, and 112i may be displaced from the distal ends of branch members 108a, 108b, 108c, and 108d by a distance equal to the sum of twice the distance of 450, and distance 460. Distance 460 may represent the longitudinal distance between bends 112*d* and 113*d* and a distal most point along movable members 112 and 113 where legs 112*a*, 112*g*, 113*a*, and 113*g* are unable to separate from one another.

Once bends 112*d* and 113*d* are engaged with the proximal ends of branch members 108*a*-*d*, legs 112*c*, 113*e*, 113*c*, and 112*e* may be fixed with respect to branch members 108*a*, 108*b*, 108*c*, and 108*d*, respectively. That is, the legs 112*c*, 113*e*, 113*c*, and 112*e* may move in the same manner (i.e., coextensively) with respective branch members 108*a*, 108*b*, 108*c*, and 108*d* when bends 112*d* and 113*d* are engaged with the proximal ends of branch members 108*a*-*d*. Drive member 128 may be moved proximally to return medical device 100 to the collapsed configuration.

Movable members may be routed through various branch members in any suitable configuration such that a distance (e.g., 450) is disposed between proximal bends (e.g., 112*d* and 113*d*) of the movable members, and the proximal ends of the branch members. For example, a medical device 800 may include movable members 812 and 813 that are routed through branch members 808*a*-*d* in the example shown by FIGS. 13-16. Movable members 812 and 813, and branch members 808*a*-*d*, may be substantially similar to movable members 112 and 113, and branch members 108*a*-*d*, respectively.

Referring to FIGS. 13-16, first leg 812*a* of movable member 812 may extend distally from the drive member 128, and may enter the proximal end of a branch member 808*a*. The first leg 812*a* may extend distally through branch member 808*a*, and may exit the distal end of the branch member 808*a*. There, the first leg 812*a* may transition into a bend 812*b*. The bend 112*b* may transition into a second leg 812*c*. The second leg 812*c* may enter the distal end of a branch member 808*d*. The second leg 812*c* may extend proximally through branch member 808*d*, and may exit the proximal end of branch member 808*d*. There, the second leg 812*c* may transition into a bend 812*d* that encompasses a middle portion (including the midpoint) of movable member 812. Bend 812*d* may transition into a third leg 812*e*. The third leg 812*e* may enter the proximal end of a branch member 808*b*. The third leg 812*e* may extend distally through branch member 808*b*, and may exit the distal end of branch member 808*b*. There, third leg 812*e* may transition into bend 812*f*. Bend 812*f* may transition into fourth leg 812*g*. The fourth leg 812*g* may extend proximally through a branch member 808*c*, and may exit the proximal end of branch member 808*c*. There, fourth leg 812*g* may be coupled to drive member 128.

First leg 813*a* of movable member 813 may extend distally from the drive member 128, and may enter the proximal end of branch member 808*b*. The first leg 813*a* may extend distally through branch member 808*b*, and may exit the distal end of the branch member 808*b*. There, the first leg 813*a* may transition into a bend 813*b*. The bend 813*b* may transition into a second leg 813*c*. The second leg 813*c* may enter the distal end of branch member 808*a*. The second leg 813*c* may extend proximally through branch member 808*a*, and may exit the proximal end of branch member 808*a*. There, the second leg 813*c* may transition into a bend 813*d* that encompasses a middle portion (including the midpoint) of movable member 813. Bend 813*d* may transition into a third leg 813*e*. The third leg 813*e* may enter the proximal end of branch member 808*c*. The third leg 813*e* may extend distally through branch member 808*c*, and may exit the distal end of branch member 808*c*. There, third leg 813*e* may transition into bend 813*f*. Bend 813*f* may transition into fourth leg 813*g*. The fourth leg 813*g* may extend proximally through branch member 808*d*, and may exit the proximal end of branch member 808*d*. There, fourth leg 813*g* may be coupled to drive member 128.

Thus, in the example shown in FIGS. 13-16, each of branch members 808*a*-*d* may have a portion of two different movable members disposed therethrough (e.g., one of each movable members 812 and 813 may be disposed through each branch member 808*a*-*d*).

Medical device 800 may be opened and closed in a substantially similar manner as medical device 100 described with reference to FIGS. 7-12. For example, a distance 850 (shown only in FIG. 13, substantially similar to distance 450) may be determined by the distance between the proximal ends of branch members 808*a*-*d* and bends 812*d* and 813*d*. Thus, the entireties of movable members 812, 813 may move longitudinally, and with respect to branch members 808*a*-*d*. As movable members 812 and 813 are moved distally by distances 850 and 860, bridges of medical device 800 (not shown, but substantially similar to bridges 112*h*, 112*i*, 113*h*, and 113*i* of FIG. 7) may extend distally from the distal ends of branch members 808*a*-*d* by a distance equal to the sum of twice the distance 850, and distance 860.

The presence of distance 450 between the proximal ends or branch members 108*a*-*d* and bends 112*d* and 113*d* may facilitate the reciprocal movement of medical device 100 between the collapsed and expanded configurations. That is, the presence of distance 450 may reduce an initial amount of force required move medical device 100 from the collapsed configuration. In some examples, distance 450 may thus allow basket 106 to open with greater ease by increasing the distance that movable members 112 extend distally from branch members 108, thereby reducing the clamping force of the distal ends of movable members 112. The reduction in clamping force may facilitate the outward radial expansion of movable members 112. The presence of distance 450 may also permit medical device 100 to capture smaller fragments within only the portion of movable members 112 extending distally from branch members 108. The distal ends of movable members 112 may more securely capture smaller fragments than branch members 108 alone. Distance 850 may function in a similar manner for medical device 800.

The disclosed retrieval devices may be utilized in any suitable application requiring the capture and removal of materials from the body. Any aspect set forth in any example may be used with any other example set forth herein. The devices may be used in any suitable medical procedure, may be advanced through any suitable body lumen and body cavity, and may be used to remove material from any suitable body portion. For example, the devices described herein may be used through any natural body lumen or tract, including those accessed orally, vaginally, rectally, nasally, urethrally, or through incisions in any suitable tissue.

The disclosed devices may be configured to capture fragments having dimensions of about 3 French or smaller. In some examples, the disclosed medical devices may be able to capture and release smaller stones having diameters from 1 millimeter to 12 millimeters. In some examples, a user may want to reposition larger stones from the lower calyx to the upper calyx of the kidney to be broken with a laser before removing them through a small diameter of the ureter. The stones may be removed in front of a scope, as opposed to through scope channel to prevent damage to a scope channel. When stones are removed, both an endoscope and the retrieval device may be removed from the human body. In some examples, a guide sheath for a ureteroscope may be used to guide the ureteroscope and retrieval device back to a previous position or to a new position to capture additional stones, and protect a ureter wall during stone removal. While moving from the extended and expanded state to the retracted and contracted state, retrieval devices of the present disclosure may ligate larger stones and capture smaller stones within the grasper portion 52.

It will be apparent to those skilled in the art that various modifications and variations can be made in the disclosed systems and processes without departing from the scope of the disclosure. For example, the retrieval device disclosed could include more than three support members, such as four or five support members, and an equal number or less movable members. Other examples of the disclosure will be apparent to those skilled in the art from consideration of the specification and practice of the features disclosed herein. It is intended that the specification and examples be considered as exemplary only.

I claim:

1. A retrieval device having a contracted state and an expanded state, comprising:
    at least three support members each having a lumen, a fixed proximal end, and a movable distal end;
    at least two movable members movable relative to the support members, each movable member including a first end and a second end and extending distally through a lumen of a support member and proximally through a lumen of a different support member, wherein the first ends and the second ends of the movable members are movable relative to each of the at least three support members, and the first ends extend proximally of the second ends when the retrieval device is in the contracted state, and in the expanded state, portions of the at least three support members and portions of the at least two movable members move radially outward relative to a central longitudinal axis of the retrieval device; and
    a stop located at the second end of at least one movable member to restrict movement of the second end after moving a distance distally during movement of the retrieval device toward the expanded state, wherein the portions of the at least three support members and the portions of the at least two movable members move radially outward relative to the central longitudinal axis of the retrieval device only after:
        the stop has moved the distance distally, and
        after the stop has moved the distance distally, the first ends of the movable members are moved further distally.

2. The retrieval device of claim 1, wherein the at least two movable members include three movable members.

3. The retrieval device of claim 1, wherein the stop includes a coupling securing the second ends of the at least two movable members together, and the coupling includes a tube surrounding the second ends.

4. The retrieval device of claim 1, wherein each of the movable members includes a preformed U-shaped bend located distally of the movable distal ends of the support members, the U-shaped bend urges the support members toward the contracted state, the U-shaped bend is located the distance from the movable distal end when the movable stop is abutting the fixed proximal end of at least one of the support members, and the movable members form a first stage grasper when the U-shaped bend is located the distance from the movable distal end.

5. The retrieval device of claim 1, wherein the support members extend generally parallel to one another during movement of the stop distally toward the expanded state.

6. The retrieval device of claim 1, further including a sheath fixedly coupled to the proximal end of each of the support members, the sheath extending proximally to encompass at least a portion of the movable members.

7. The retrieval device of claim 1, further including an actuator coupled to the first ends of each of the movable members, the actuator configured to move the first ends of the movable members proximally and distally relative to the at least three support members.

8. A retrieval device having a contracted state and an expanded state, comprising:
    at least three tubes each having a lumen, a fixed proximal end, and a movable distal end;
    at least three wires movable relative to the tubes, each wire including a first end and a second end and extending distally through a lumen of a tube and proximally through a lumen of a different tube;
    an actuator coupled to the first ends of each of the wires, the actuator configured to move the first ends of the wires proximally and distally relative to the at least three tubes; and
    a stop for the wires, the stop including a coupling of the second ends of each of the wires together at a spaced distance from the fixed proximal ends of the tubes, wherein:
    while the retrieval device is in the contracted state, initial movement of the actuator distally also moves the stop distally until the stop is prevented from moving further distally; and
    after the stop is prevented from moving further distally, further distal movement of the actuator causes the movable distal ends of the at least three tubes, and the at least three wires to move radially outward.

9. The retrieval device of claim 8, wherein the coupling of the second ends includes securing the second ends in a tube coupler.

10. The retrieval device of claim 8, wherein the stop is located the spaced distance from the fixed proximal ends of the tubes when the device is in a fully contracted state, and the spaced distance is reduced during movement of the device toward the expanded state.

11. The retrieval device of claim 8, wherein the first end is located proximally of the second end when the retrieval device is in the contracted state.

12. The retrieval device of claim 8, wherein each of the wires includes a preformed U-shaped bend located distally of the movable distal ends of the tubes.

13. The retrieval device of claim 12, wherein the U-shaped bend urges the tubes toward the contracted state.

14. The retrieval device of claim 13, wherein the U-shaped bend is located a fixed distance from the stop and moves with the stop.

15. The retrieval device of claim 14, wherein the wires form a first stage grasper during initial movement toward the expanded state.

16. The retrieval device of claim 8, wherein the tubes extend generally parallel to one another during movement of the movable stop toward the expanded state.

17. The retrieval device of claim 8, wherein the actuator and the stop are separate components indirectly connected to one another by the at least three wires.

18. A method for retrieving an object using a retrieval device including at least three tubular support members each having a fixed proximal end and a movable distal end; at least two movable members movable relative to the support members, each movable member including a first end and a second end and extending distally through a support member and proximally through a different support member; an actuator coupled to the first end of each movable member, and a stop located at the second end of at least one movable member, the method comprising:
- sliding the actuator to move the first and second ends of the movable members distally until the stop restricts further movement of the second ends; and
- further sliding the actuator after the stop restricts further movement of the second ends to move the first ends of the movable members distally to expand the movable distal ends of the support members radially outward.

19. The method of claim 18, wherein sliding the actuator to move the first and second ends of the movable members includes sliding the actuator distally, and further sliding the actuator after the stop restricts further movement of the second ends includes further sliding the actuator distally.

20. The method of claim 19, wherein the actuator and the stop are separate components indirectly connected to one another by the at least two movable members.

\* \* \* \* \*